United States Patent [19]

Hubbard et al.

[11] Patent Number: 4,617,017

[45] Date of Patent: * Oct. 14, 1986

[54] PERSONAL CATHETER LEG STRAP

[75] Inventors: Vance M. Hubbard, Euless; Welton K. Brunson, Bedford, both of Tex.

[73] Assignee: Tencol, Inc., Fort Worth, Tex.

[*] Notice: The portion of the term of this patent subsequent to Feb. 18, 2003 has been disclaimed.

[21] Appl. No.: 777,542

[22] Filed: Sep. 18, 1985

Related U.S. Application Data

[63] Continuation-in-part of Ser. No. 479,671, Mar. 28, 1983, Pat. No. 4,571,245.

[51] Int. Cl.$^4$ ............................................. A61M 25/02
[52] U.S. Cl. ............................. 604/179; 128/DIG. 26
[58] Field of Search ...................... 604/174, 179, 180; 128/DIG. 26, 133

[56] References Cited

U.S. PATENT DOCUMENTS

| | | | |
|---|---|---|---|
| 3,430,300 | 3/1969 | Doan | 604/180 X |
| 4,088,136 | 5/1978 | Hasslinger et al. | 604/179 |
| 4,096,863 | 6/1978 | Kaplan et al. | 604/179 |
| 4,445,894 | 5/1984 | Kovacs | 604/179 |
| 4,548,200 | 10/1985 | Wapner | 604/179 X |
| 4,569,348 | 2/1986 | Hasslinger | 604/179 |

Primary Examiner—Dalton L. Truluck
Attorney, Agent, or Firm—Jerry W. Mills; Gregory M. Howison

[57] ABSTRACT

A personal catheter leg strap (10) for the securement of any one of a plurality of differently sized catheter tubes (32) includes a first section (12) of a gauze type material and a second section (14) of elastic type material joined together at a junction (16) for wrapping about a limb. A Velcro-type strip (30) attaches the two free ends of the first and second portions together. A catheter tube securing strap (22) is attached at one end thereof to the junction (16) and has two portions (24) and (26), of which the portion (26) is narrower throughout its length. An orifice (28) is disposed in the broad portion (24) and is dimensioned such that the entire length of the narrow portion (26) is insertable therein. The securing strap (22) has a free end thereof wrapped around a catheter tube (32) one revolution and inserted through the orifice (28). Within the one revolution, protruding members (29) protrude inwardly into the exterior surface (36) of tube (32), firmly securing it to the strap (22). The strap (22) is wrapped an additional approximately one-half revolution about the catheter tube (32) and is attached at any of an infinate number of locations on the surface (20) with the Velcro-type surface of the securing strap (22).

4 Claims, 5 Drawing Figures

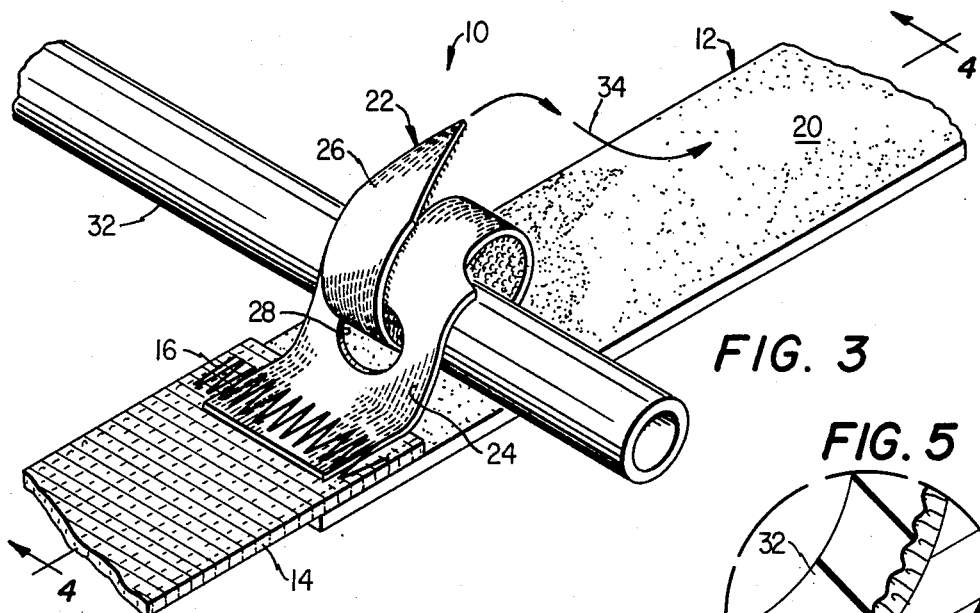

4,617,017

PERSONAL CATHETER LEG STRAP

CROSS REFERENCE TO RELATED APPLICATION

This application is a continuation-in-part of copending application Ser. No. 479,671, filed on Mar. 28, 1983, now U.S. Pat. No. 4,571,245 issued Feb 18, 1986.

TECHNICAL FIELD

The invention pertains in general to tubular securing devices and, more particularly, to a device for securing a catheter tube on a portion of the anatomy adjacent the catheter insertion point.

BACKGROUND OF THE INVENTION

Catheter securing devices provide a very useful function in immobilizing the catheter tube after insertion of the catheter. Normally these devices secure the catheter to a limb in close proximity to the insertion point of the catheter to provide an immobilizing function to enable a patient some additional degree of mobility with the catheter inserted. In addition to the immobilizing function, the catheter securing device also must provide a certain degree of comfort to the patients since these devices are normally attached for some length of time.

An example of a catheter securing device is disclosed in U.S. Pat. No. 4,096,863 issued to Kaplan et al. The Kaplan device illustrates a strap that is operable to be secured around the limb and having a secondary strap attached thereto for wrapping about the catheter tube. The secondary strap has a Velcro-type material attached thereto for mating with a second Velcro-type material disposed on the surface of the primary strap wrapped about the limb. The secondary strap wraps about the catheter tube and loops back through a metal ring. This metal ring allows the secondary strap to be tightened around the catheter over a large portion of the circumference thereof. However, a portion of the catheter tube is disposed adjacent the opening of the metal ring thereby exhibiting a tendency to "pinch" the catheter tube. As the secondary strap is tightened around the catheter tube, the catheter tube tends to bulge through the metal ring thereby increasing the pinching effect.

A further example of a catheter securing device is disclosed in U.S. Pat. No. 4,088,136 issued to Hasslinger, et al. Hasslinger illustrates a catheter leg strap having a securing band of Velcro-type material on one side thereof, the securing band being attached to one free end of the leg strap. Hasslinger disposes a circular hole some distance back from the free end of the leg strap on which the Velcro-type securing band is attached. The portion of the leg strap intermediate the free end and the hole consists of a padded material that is designed to squeeze the catheter tube and thus secure it in place. The terminal Velcro securing band is used to both secure the catheter leg to the leg strap and also to secure the leg strap to the leg. The Hasslinger design has two drawbacks. First, the portion of the leg strap between the circular orifice and the Velcro securing band is tapered, such that when the securing band and the terminal portion is inserted into the orifice and drawn around the catheter tube, the tapered portion will eventually abut up against the orifice without being able to be pulled further through the hole. Hasslinger is thus designed for use only with a specified diameter of a catheter tube. Smaller diameter catheter tubes cannot be securely fastened to Hasslinger's catheter leg strap, causing undesirable movement in relation thereto. The other drawback of the Hasslinger device is that a padded element is used to secure the catheter tube to the leg strap. By putting equal pressure on all sides of the catheter tube, the catheter tube is prone to slippage with respect to the leg strap.

In view of the prior art, there exists a need for a catheter tube securing apparatus that firmly holds any of a plurality of differently sized catheter tubes in place with a roughly uniform restriction about the entire circumference of the tube.

SUMMARY OF THE INVENTION

The present invention disclosed and claimed herein comprises an apparatus for securing a tubular device. The apparatus includes a first resilient strip for providing a mounting surface with a fastening material attached to oneend for fastening to the other end thereof for attaching the first resilient strip to a selected area where the tubular device is to be secured. A second resilient strip is attached at one end thereof to the first resilient strip. The second resilient strip has a first portion with a first width and a second portion with a second and wider width. The second portion is adjacent the first resilient strip and has an orifice disposed through the surface thereof dimensioned to receive the first portion. The free end of the first portion is operable to wrap around the tubular device at least one revolution and insert through the orifice in the second portion. Velcro-type protruding members disposed on one surface of the second portion protrude inwardly into the surface of the catheter tube through the one revolution, causing the catheter tube to be more firmly gripped by the second portion. The free end is then wrapped essentially an additional one-half revolution about the tube and attached to the surface of the first resilient strip. The apparatus disclosed and claimed herein can firmly secure tubular devices of a range of diameters.

BRIEF DESCRIPTION OF THE DRAWING

For a more complete understanding of the present invention and the advantages thereof, reference is now made to the following description taken in conjunction with the accompanying Drawings in which:

FIG. 1 is a plan view of the inner surface of the catheter tube securing device;

FIG. 2 illustrates a plan view of the outer surface of the catheter tube securing device;

FIG. 3 illustrates a perspective view of the catheter securing device with the catheter tube in place;

FIG. 4 illustrates a cross sectional view of the device in FIG. 3 taken along line 4-4 thereof; and FIG. 5 illustrates a detail of FIG. 4, showing the indentations made by protruding Velcro-type members into the exterior surface of a yieldable catheter tube.

DETAILED DESCRIPTION OF THE INVENTION

Referring now to FIGS. 1 and 2, there are illustrated plan views of both sides of a catheter tube holder 10. The tube holder 10 is divided into two sections 12 and 14 that are attached together at one end thereof by a seam 16. The section 14 is fabricated of an elastic webbing material which is stretchable in a lengthwise direction but has a relatively defined dimension across its width. The section 12 is fabricated of a gauze type material having a woven surface 18 on the bottom side thereof, as depicted in FIG. 1, and a fibrous surface 20 of the top side thereof, as depicted in FIG. 2. This fibrous surface can be a cotton or similar type material.

A securing strap 22 is attached at one end thereof to the seam 16 and oriented such that it lays essentially parallel to the surface 20 of the section 12. The securing strap 22 is divided into a broad portion 24 and a narrow portion 26, the broad portion 24 being disposed adjacent the seam 16. The broad portion 24 of the securing strap 22 has an orifice 28 with a diameter essentially equal to or slightly larger than the width of the narrow portion 26. As will be described below, the narrow portion 26 is dimensioned to be inserted into the orifice 28. It should be understood that, although the orifice 28 is shown as a circle, it can be configured in any number of ways. For example, one configuration of the orifice could be a slot that is parallel to the seam 16.

The surface of the securing strap facing the surface 20 of the section 12 has a plurality of small protruding members 29 disposed thereon to provide a Velcro-type material. Protruding members 29 can be in the form of stalked disks, lollipop-like elements or hook-like members as illustrated. Protruding members 29 are operable to mate with the fibrous material of the surface 20 to interconnect thereto. This type of fastening device allows the securing strap 22 to be firmly fastened to the surface 20 of the section 12. "Velcro" is a trademark for an attachment device having small hook-shaped, lollipop or stalked disc members on one surface and loose fibers on a mating surface. When these two surfaces are joined, the protruding members 29 "tangle" with the fibrous material to form a bond therebetween which is easily separable.

A Velcro-type strip 30 is attached to the end of the section 14 diametrically opposite the seam 16. The Velcro-type strip 30 has a plurality of hooklike or other protruding elements disposed on one surface thereof and oriented such that they mate or interlock with the fibrous material of the surface 20 when the end of the section 14 is wrapped around a limb or other such surface to meet with the end of the section 12.

Referring now to FIG. 3, there is illustrated a perspective view of the catheter tube holder 10 with the securing strap 22 loosely wrapped about a catheter tube 32. To secure the catheter tube 32, the tube 32 is placed between the underside of the securing strap 22 and also between the strap 22 and the surface 20. The free end of the securing strap 22 is then wrapped about the tube 32 and inserted through the orifice 28. This effectively results in one revolution of the securing strap 22 around the tube 32. The free end of the securing strap 22 is then wrapped an additional one-half revolution, more or less, around the tube 32 in the direction of arrows 34 for attachment to the surface 20.

The secured position of the securing strap 22 about the tube 32 is better illustrated in the cross sectional view in FIG. 4 taken along lines 4—4 of FIG. 3. As illustrated, the tube 32 is secured by the securing strap 22 wrapped thereabout approximately one and one-half revolutions and attached at the free end thereof to the fibrous material on the surface 20. It is important to note that the securing strap 22 is wrapped about the tube 32 in such a manner that there is resulting downward force on the tube directed toward the surface 20. This, in combination with the one and one-half revolutions around the tube, adequately secures the tube 32 against the surface 20. The circumventing of the tube 32 is an important aspect of the present invention in that "pinching" of the tube 32 is prevented. This pinching can result in constriction of the tube through the secured portion. By circumventing the tube, it is not possible to constrict the passage therethrough without substantially deforming the tube 32. However, if the forces are unevenly distributed, the tube 32 exhibits a tendency to take on an oblique shape. By spreading the forces evenly, this is prevented.

Securing strap 22 is operable to secure any of a variety of catheter tubes having differing diameters. The tube sizes that can be effectively secured by the invention range from 12 fr., having a diameter of 4.0 millimeters, to 30 fr., having a diameter of 10.0 millimeters. In order to secure a relatively large diameter catheter tube, such as a catheter tube of the 30 fr. size, more of securing strap 22 is wrapped around tube 32 and narrow portion 26 is attached to fibrous surface 20 at a point somewhat closer to seam 16 than shown. In order to secure a catheter tube having a relatively narrow diameter, such as 12 fr. catheter tube, less of securing strap 22 is wrapped around catheter tube 32, and the place of attachment of narrow portion 26 to surace 20 is further away from seam 16 than as shown in FIG. 4. Since narrow portion 26 can attach at any of an infinite number of positions along surface 20, any of an infinite number of sizes of catheter tubes within a specified range can be secured by using the invention.

FIG. 4 also shows that protruding members 29 are directed inwardly into the exterior surface 34 of catheter tube 32. The relationship of protruding members 29 with respect to exterior surface 34 is more clearly shown in FIG. 5, which is a detail of FIG. 4.

In FIG. 5, protruding members 29, here shown as hook-like members, protrude inwardly into exterior surface 34 in order to create a plurality of indentations 36 in the yieldable surface of catheter tube 32. The effect shown in FIG. 5 occurs wherever the catheter tube being secured has an at least partially yieldable surface, such as the commonly used plastic catheter tubes. The interaction between protruding members 29 and indentations 36 creates a firm securement of tube 32 to securing strap 22. Indentations 36 and protruding members 29 prevent the rotation of tube 32 within securing trap 22 and also prevent axial slippage in relation thereto. This method of gripping tube 32 has proved superior to gripping by a smooth surface, as the gripping forces applied in the invention are not completely uniformly distributed on the surface. Nevertheless, the gripping action of protruding members 29 does not significantly alter the interior shape of tube 32, and thus has no significant impact on the cross-sectional area available for fluid flow.

In summary, there has been provided a catheter tube holder that includes a strap formed of an elastic portion and a fibrous portion that is held together around a limb by a Velcro-type fastener. A securing strap is attached at one end thereof to the junction of these two sections and dimensioned to have the distal, free portion thereof a narrower, width than the proximal, attached portion. The distal, free portion is operable to wrap around the catheter tube one revolution and insert through an orifice in the wider section of the securing strap. The free end of the securing strap is then wrapped about an additional approximately one-half revolution about the catheter tube and attached to the surface of the fibrous section with a Velcro-type fastener. The securing strap can secure catheter tubes of varying diameters, as the distal, free portion is narrow throughout its length and can be attached to the fibrous surface at an infinite number of positions. The securing strap is wrapped about the catheter tube in such a manner to cause a resulting downward force on the catheter tube to thereby hold it firmly against the surface of the strap.

Although a preferred embodiment has been described in detail, it should be understood that various changes, substitutions and alterations can be made therein without departing from the spirit and scope of the invention as defined by the appended claims.

What is claimed is:

1. Apparatus for securing any one of a plurality of differently sized catheter tubes to a portion of the anatomy of a patient adjacent a catheter insertion point, comprising:
   a strap for wrapping about the desired portion of the anatomy of the patient, said strap having a first elastic portion for stretching and a second portion having a layer of fibrous material disposed on one side for receiving a Velcro-type attaching layer, said first and second portions each having an end joined to each other at a junction, said first and second portions each having a free end;
   a strip of Velcro-type material attached to the free end of said first portion for mating with the free end of said second portion on said layer of fibrous material to form an attachment theretbetween;
   a securing band attached at said junction having Velcro-type protruding members disposed on one side thereof, said securing band including a first portion having a circular orifice disposed therethrough adjacent the attached end and
   a second portion integrally attached to said first portion proximate the orifice, the width of said second portion being less than the width of said first portion and being less than the diameter of said orifice through the entire length of said second portion;
   said securing band operable to wrap around any one of a plurality of differently sized catheter tubes one revolution for insertion of said second portion through said orifice and further wrap around said one of said catheter tubes about one-half revolution for attachment of said protruding members to the fibrous material on the surface of said strap at any of a plurality of locations such that said one of said catheter tubes is secured against the surface of said strap vertically and laterally by said securing band providing a downward force on the catheter tube directed toward the strap , means for preventing axial and rotational movement of said tube formed on said one side of said securing band.

2. The apparatus of claim 1 adapted to secure a yieldable catheter tube, wherein:
   said means for preventing comprise said Velcro-type protruding members , said protruding members protruding inwardly into the surface of the yieldable catheter tube through said one revolution to create indentations in the exterior surface of the catheter tube in order to firmly secure the tube to the securing band.

3. Apparatus for securing a yieldable catheter tube to a portion of the anatomy of a patient adjacent a catheter insertion point, comprising:
   a strap for wrapping about the desired portion of the anatomy of the patient, said strap having a first elastic portion for stretching and a second portion having a layer of fibrous material disposed on one side for receiving a Velcro-type attaching layer, said first and second portions each having an end joined to each other at a junction, said first and second portions each having a free end;
   a strip of Velcro-type material attached to the free end of said first portion for mating with the free end of said second portion on said layer of fibrous material to form an attachment therebetween;
   a securing band attached at said junction having Velcro-type protruding members disposed on and completely covering one side thereof, said securing band attached at said junction so as to lie parallel with said second portion when not in use so that said protruding members face downward, said securing band including a first portion having a circular orifice disposed therethrough adjacent the attached end and a second portion integrally attached to said first portion proximate the orifice, the width of said second portion being less than the width of said first portion and being less than the diameter of said orifice through the entire length of said second portion;
   said securing band operable to wrap around the yieldable catheter tube one revolution for insertion of said second portion through said orifice, said protruding members providing means for preventing axial and rotational movement of the tube leg protruding inwardly into the external surface of the yieldable catheter tube to create indentations therein to firmly secure the tube to the securing band; and
   said securing band further wrapping around the catheter tube about one-half revolution for attachment of protruding members on a distal part of the surface of said securing band to the fibrous material on the surface of said strap such that said catheter tube is secured against the surface of said strap vertically and laterally by said securing band providing a downward force on the catheter tube directed toward the strap.

4. The apparatus of claim 3, wherein said Velcro-type protruding members are hook members.

* * * * *

UNITED STATES PATENT AND TRADEMARK OFFICE
CERTIFICATE OF CORRECTION

PATENT NO. : 4,617,017
DATED : October 14, 1986
INVENTOR(S) : Vance M. Hubbard and Welton K. Brunson It is certified that error appears in the above-identified patent and that said Letters Patent is hereby corrected as shown below:

Assignee: "Tencol, Inc." should be --Tecnol, Inc.--

Col. 5, line 28, "theretbetween" should be --therebetween--.

Signed and Sealed this

Third Day of March, 1987

Attest:

DONALD J. QUIGG

Attesting Officer

Commissioner of Patents and Trademarks